US012788273B2

(12) United States Patent
Takatori et al.

(10) Patent No.: US 12,788,273 B2
(45) Date of Patent: Nov. 10, 2026

(54) AIRWAY ADAPTER

(71) Applicant: NIHON KOHDEN CORPORATION, Tokyo (JP)

(72) Inventors: Fumihiko Takatori, Tokorozawa (JP); Yuya Baba, Tokorozawa (JP); Kazumasa Ito, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 362 days.

(21) Appl. No.: 18/539,461

(22) Filed: Dec. 14, 2023

(65) Prior Publication Data

US 2024/0206764 A1 Jun. 27, 2024

(30) Foreign Application Priority Data

Dec. 23, 2022 (JP) ................................. 2022-206466

(51) Int. Cl.
*A61B 5/097* (2006.01)

(52) U.S. Cl.
CPC .......... *A61B 5/097* (2013.01); *A61B 2562/18* (2013.01)

(58) Field of Classification Search
CPC ..... A61B 5/097; A61B 2562/18; A61B 5/087; A61B 5/0873; A61M 16/085; A61M 16/0808; A61M 16/0875; A61M 16/08; A61M 2205/123; A61M 16/0475; A61M 2205/3306
USPC .......................................................... 600/543
See application file for complete search history.

(56) References Cited

U.S. PATENT DOCUMENTS

| | | | | | |
|---|---|---|---|---|---|
| 6,044,843 | A * | 4/2000 | O'Neil | A61M 16/08 | 128/207.14 |
| 6,216,692 | B1 * | 4/2001 | Todokoro | A61M 16/08 | 128/204.23 |
| 2006/0037613 | A1 * | 2/2006 | Kwok | A61M 16/16 | 128/203.26 |
| 2006/0144399 | A1 * | 7/2006 | Davidowski | A61M 16/06 | 128/205.12 |
| 2018/0372347 | A1 * | 12/2018 | Carlson | F24F 13/30 | |

FOREIGN PATENT DOCUMENTS

| | | | |
|---|---|---|---|
| EP | 728441 | A2 * | 8/1996 |
| JP | H08233699 | A * | 9/1996 |
| JP | 2015-040770 | A | 3/2015 |
| JP | 2015-163275 | A | 9/2015 |

OTHER PUBLICATIONS

Japanese Office Action issued in Japanese Patent Application No. 2022-206466 dated Apr. 7, 2026.

* cited by examiner

*Primary Examiner* — Brian L Casler
(74) *Attorney, Agent, or Firm* — McDonald Hopkins LLC

(57) ABSTRACT

An airway adapter includes a measurement flow path through which at least one of expired air or inhaled air of a subject passes through. A water absorption member is provided in a lower portion of the measurement flow path in a state where the airway adapter is placed. The water absorption member is exposed to an outside, and is configured to discharge water to the outside.

14 Claims, 8 Drawing Sheets

AIRWAY ADAPTER

CROSS-REFERENCE TO RELATED APPLICATIONS

This application is based on and claims priority under 35 USC 119 from Japanese Patent Application No. 2022-206466 filed on Dec. 23, 2022, the entire content of which is incorporated herein by reference.

TECHNICAL FIELD

The presently disclosed subject matter relates to a sensor configured to detect a predetermined respiratory gas (carbon dioxide, oxygen, laughing gas, volatile anesthesia gas, or the like) contained in respiratory air of a living body, and an airway adapter detachably attached to the sensor and formed with a passage through which the respiratory air of the living body pass.

BACKGROUND ART

A measurement flow path through which a respiratory air of a subject pass is formed in the airway adapter, and a predetermined respiratory gas contained in the respiratory air is measured. For example, in an airway adapter for measuring a carbon dioxide concentration, an optical axis that connects a light emitting unit and a light receiving unit provided in a sensor is disposed so as to cross the measurement flow path. Infrared light emitted from the light emitting unit is received by the light receiving unit, and a signal corresponding to an intensity of the received light is output from the sensor. As the carbon dioxide concentration in the respiratory air increases, the infrared light is more strongly absorbed and the intensity of the received light decreases. Therefore, the carbon dioxide concentration contained in the respiratory air of the subject can be measured by monitoring an intensity of the signal output from the sensor. Examples of such airway adapter and sensor are disclosed in JP2015-163275A.

In the measurement flow path of the airway adapter, expired air containing moisture from a body of the subject and humidified inhaled air pass, but condensation occurs in the measurement flow path and in a vicinity thereof due to a decrease in temperature or the like. Further, when the condensation stays in the measurement flow path, the infrared light is refracted by water generated by the condensation, or the like, and accurate measurement is difficult.

SUMMARY OF INVENTION

Aspects of certain non-limiting embodiments of the present disclosure address the features discussed above and/or other features not described above. However, aspects of the non-limiting embodiments are not required to address the above features, and aspects of the non-limiting embodiments of the present disclosure may not address features described above.

According to an aspect of the present disclosure, there is provided an airway adapter including:

a measurement flow path through which at least one of expired air or inhaled air of a subject passes through, in which a water absorption member is provided in a lower portion of the measurement flow path in a state where the airway adapter is placed, and the water absorption member is exposed to an outside, and is configured to discharge water to the outside.

BRIEF DESCRIPTION OF DRAWINGS

Exemplary embodiment(s) of the present invention will be described in detail based on the following figures, wherein.

DESCRIPTION OF EMBODIMENTS

Figure 1:
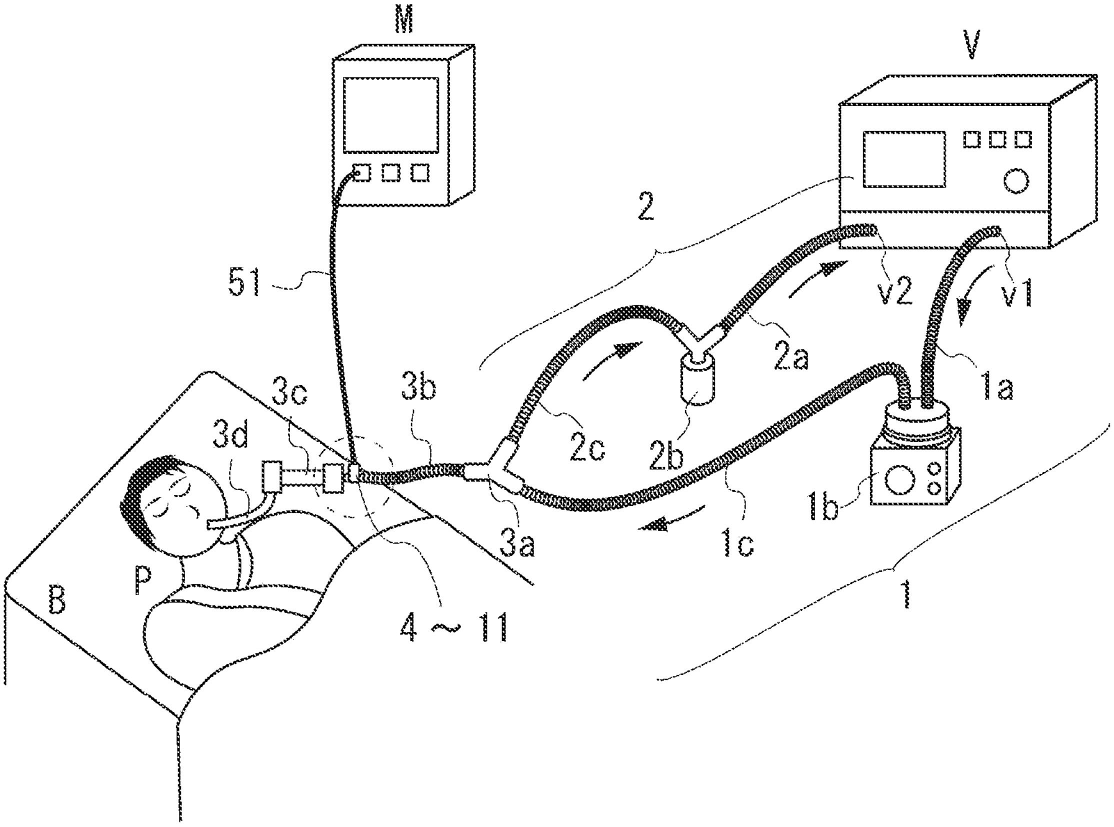
FIG. 1 illustrates a state of a respirator using an airway adapter.

FIG. 1 is commonly used in a known embodiment and each embodiment. FIG. 1 schematically illustrates a state in which a respirator V is attached to a patient P lying on a bed B. The respirator V sends a gas for inhaled air containing a large amount of oxygen to the patient P, and discharges expired air of the patient P. An inhaled air circuit 1 is connected to an inhaled air side connection portion v1 of the respirator V, and an expired air circuit 2 is connected to an expired air side connection portion v2. In the inhaled air circuit 1, a breathing tube 1*a* is connected to the inhaled air side connection portion v1 of the respirator V, and a humidifier 1*b* is connected to the breathing tube 1*a*. A breathing tube 1*c* is connected to the humidifier 1*b*, and the breathing tube 1*c* is connected to a Y-piece 3*a*. Further, in the expired air circuit 2, a breathing tube 2*a* is connected to the expired air side connection portion v2 of the respirator V, and a water trap 2*b* is connected to the breathing tube 2*a*. A breathing tube 2*c* is connected to the water trap 2*b*, and the Y-piece 3*a* is connected to the breathing tube 2*c*. The breathing tubes 1*c* and 2*c* are connected to the Y-piece 3*a*, and a flexible tube 3*b* is connected to the remaining connection portion of the Y-piece 3*a*. A connection tube 3*c* is connected to an intubation tube 3*d* via an airway adapter 4 or the like. The intubation tube 3*d* is inserted from a mouth of the patient P to a trachea.

An optical sensor 5, which is a type of sensor, is attached to the airway adapter 4 or the like. The optical sensor 5 is configured to optically measure the respiratory gas passing through the airway adapter 4 or the like. In the optical sensor 5, a received light value of the infrared light passing through the airway adapter 4 or the like is obtained, a carbon dioxide concentration is calculated from the received light value sent to a patient monitor M via wiring 51, and a measured value is monitored.

As illustrated in FIG. 1, the inhaled air supplied from the respirator V is humidified by the humidifier 1*b*. Further, the expired air discharged from the patient P also contains water vapor. Therefore, condensation occurs around the airway adapter 4 or the like exposed to a temperature lower than a body temperature.

Figure 2:
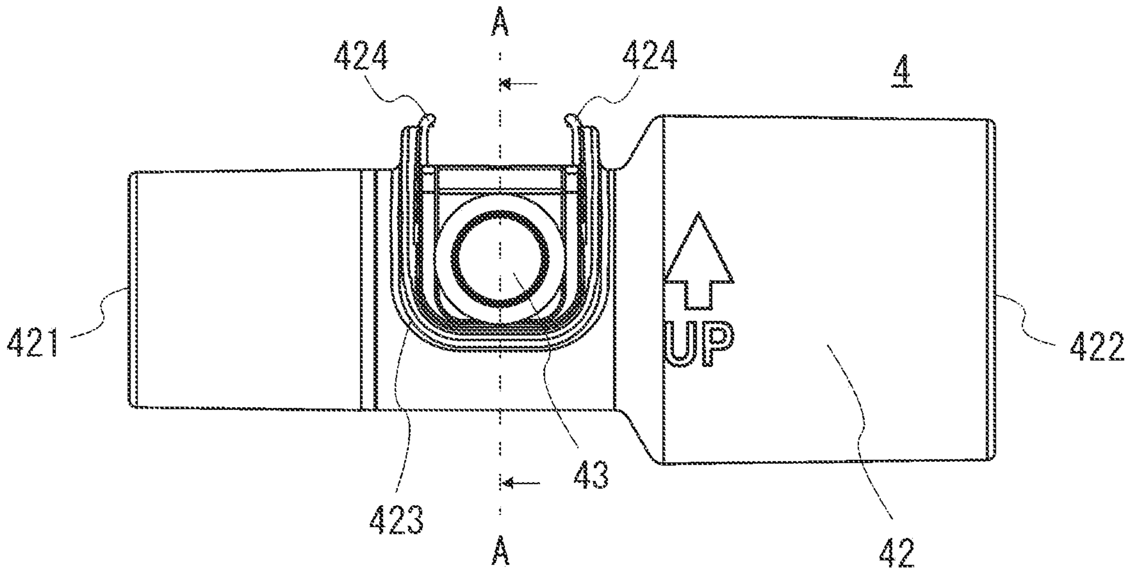
FIG. 2 is a side view of an airway adapter in the related art.
Figure 3:
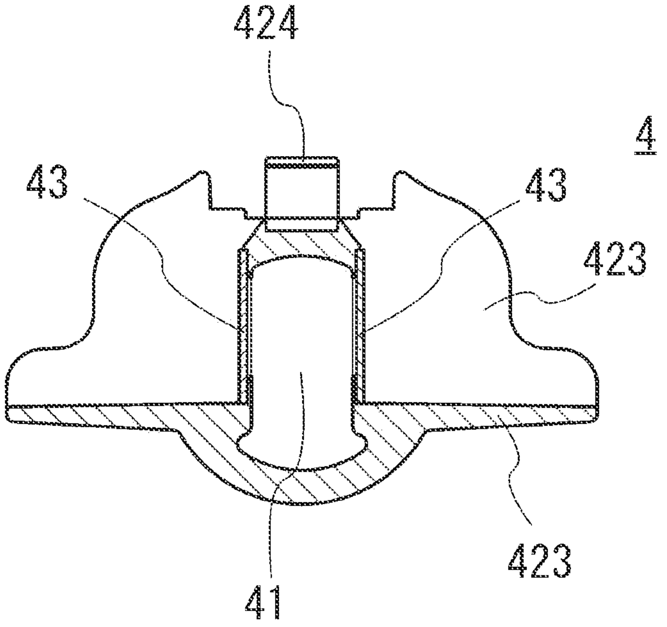
FIG. 3 is a cross-sectional view of the airway adapter in the related art.

FIG. 2 and FIG. 3 illustrate a known airway adapter 4. FIG. 2 is a side view of the airway adapter 4. FIG. 3 is a cross-sectional view taken along plane A-A in FIG. 2, and illustrates a state viewed from a direction of an arrow in FIG. 2. The airway adapter 4 may include an adapter body 42 and window portions 43. As illustrated in FIG. 3, the adapter body 42 may include a sensor holding portion 423 projecting to both sides and locking projections 424 projecting upward. The sensor holding portion 423 is formed in a U-shape to hold the optical sensor 5 inside. The sensor holding portion 423 and the locking projections 424 are used to detachably fix the optical sensor 5 to the airway adapter 4.

Further, as illustrated in FIG. 3, a measurement flow path 41 through which the respiratory air passes is formed inside the airway adapter 4. The measurement flow path 41 penetrates the adapter body 42 illustrated in FIG. 2 from a device side connection port 421 to a subject side connection port 422, and passes between the opposed window portions 43. The adapter body 42 may have openings on both sides of the measurement flow path 41. A sheet-shaped infrared light transmission resin, which is a member through which the infrared light transmits, closes the openings to form the window portions 43. The infrared light for measurement sent out from the optical sensor 5 fixed to the inside of the sensor holding portion 423 passes across the measurement flow path 41 from one window portion 43 to the other window portion 43 illustrated in FIG. 3. Since the infrared light is absorbed by carbon dioxide in the measurement flow path 41, the optical sensor 5 obtains a received light amount corresponding to a carbon dioxide concentration in the respiratory air passing through the measurement flow path 41.

The airway adapter 4 is long in an extending direction of the measurement flow path 41. The flexible tube 3*b* illustrated in FIG. 1 is connected to the device side connection port 421, and the intubation tube 3*d* is attached to the subject side connection port 422 via the connection tube 3*c*. Further, as illustrated in FIG. 3, the sensor holding portion 423 is expanded below the adapter body 42, and the airway adapter 4 is unlikely to be horizontally oriented. With this configuration, the airway adapter 4 is placed and provided above the bed B substantially in a vertical direction provided in FIG. 2 and FIG. 3.

Water generated by condensation inside and around the airway adapter 4 accumulates in a lower portion of the measurement flow path 41 illustrated in FIG. 3, inside the airway adapter 4. When the airway adapter 4 is turned in a lateral direction and is inclined, or when water is scattered in the measurement flow path 41 due to respiration, there is a possibility that water enters between the window portions 43. When water enters between the window portions 43, there is a concern that the infrared light for measurement is refracted by the water and the received light amount decreases. When the infrared light is refracted by the water and the received light amount decreases, it is difficult to accurately measure the carbon dioxide concentration.

Embodiment 1

Figure 4:
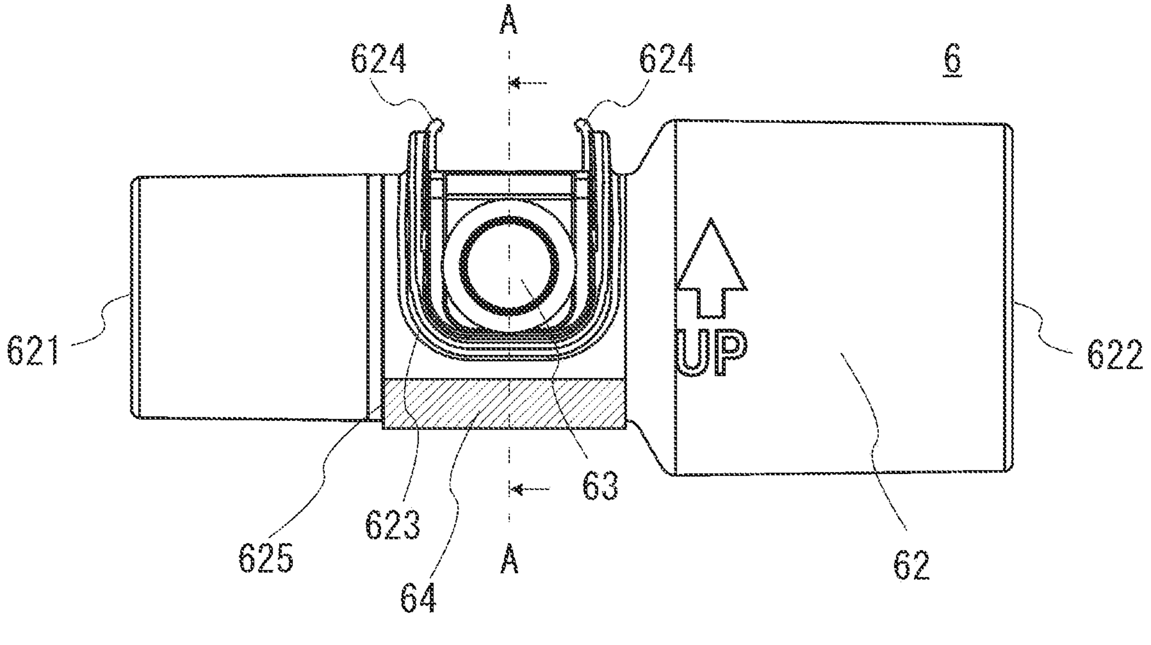
FIG. 4 is a side view of an airway adapter according to Embodiment 1.
Figure 5:
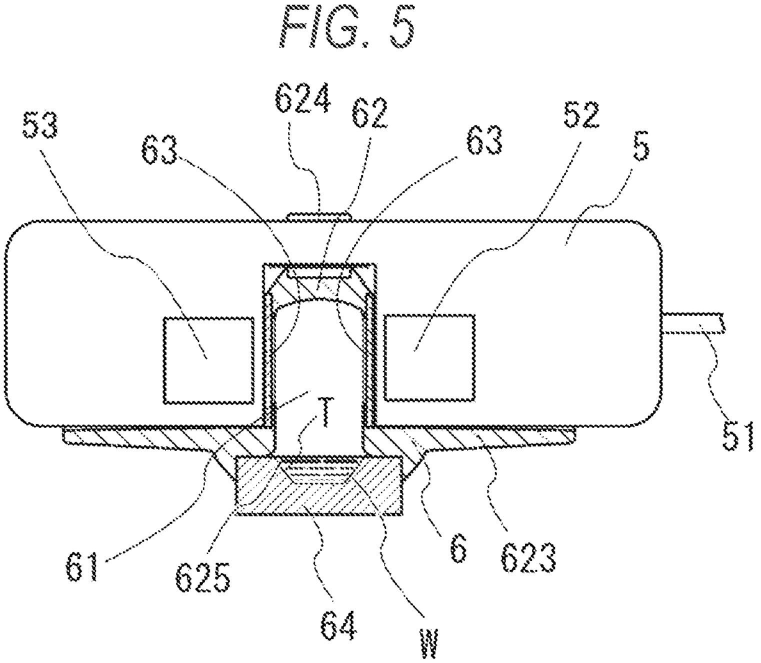
FIG. 5 is a cross-sectional view of the airway adapter according to Embodiment 1.
Figure 6:
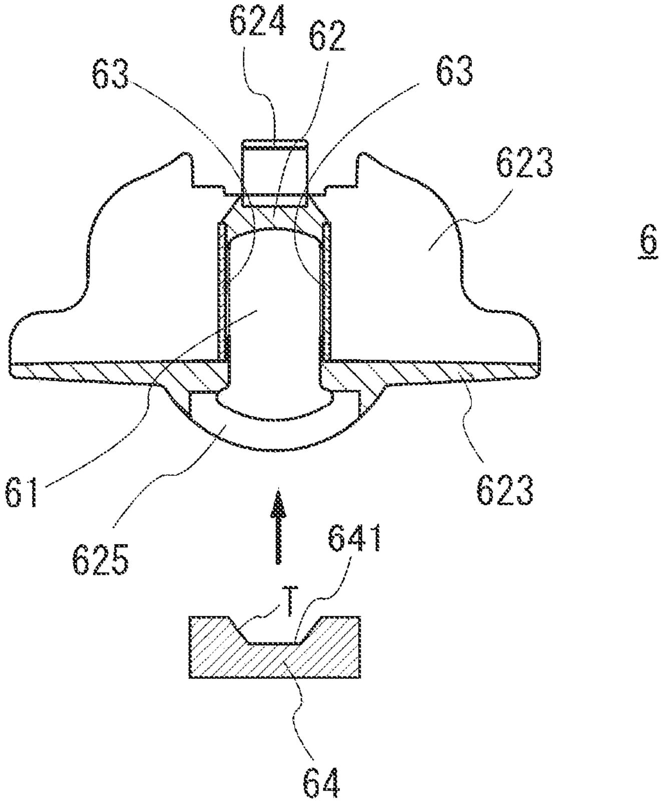
FIG. 6 is a cross-sectional view of the airway adapter according to Embodiment 1 before an opening is closed.

FIG. 4 to FIG. 6 illustrate an airway adapter 6 according to Embodiment 1. FIG. 4 is a side view of the airway adapter 6 according to Embodiment 1. FIG. 5 and FIG. 6 are cross-sectional views taken along plane A-A in FIG. 4, and illustrate a state viewed from a direction of an arrow in FIG. 4. FIG. 5 illustrates the airway adapter 6 to which the optical sensor 5 is attached, and FIG. 6 illustrates the airway adapter 6 before an opening 625 is closed. The airway adapter 6 is placed and provided above the bed B substantially in a vertical direction illustrated in FIG. 4 to FIG. 6 during provision. The airway adapter 6 according to Embodiment 1 is connected and used as illustrated in FIG. 1, same or similarly to the airway adapter 4 according to the known embodiment.

As illustrated in FIG. 4 to FIG. 6, the airway adapter 6 according to Embodiment 1 may include an adapter body 62, window portions 63, and a water absorption member 64. The adapter body 62 is made of resin. The window portions 63 are made of a resin that transmits the infrared light, and are provided on both sides of a measurement flow path 61 as illustrated in FIG. 5 and FIG. 6. As illustrated in FIG. 4 to FIG. 6, a U-shaped sensor holding portion 623 sticks out both sides of the adapter body 62, and locking projections 624 project upward.

As illustrated in FIG. 5 and FIG. 6, a measurement flow path 61 through which the respiratory air passes is formed inside the airway adapter 6. The measurement flow path 61 penetrates the adapter body 62 from a device side connection port 621 to a subject side connection port 622, and passes between the opposed window portions 63. The adapter body 62 may have openings on both sides of the measurement flow path 61. A sheet-shaped infrared light transmission resin, which is a member through which the infrared light transmits, closes the openings to form the window portions 63.

As illustrated in FIG. 1, the optical sensor 5 illustrated in FIG. 5 is connected to the patient monitor M via the wiring 51. In FIG. 5, in the optical sensor 5, a light emitting unit 52 and a light receiving unit 53 which are internal configurations are conceptually described. The optical sensor 5 is held inside the U-shaped sensor holding portion 623 in a state of straddling the measurement flow path 61. An upper portion of the optical sensor 5 is locked by the two locking projections 624, and is detachably fixed to the airway adapter 6.

In the optical sensor 5 attached to the airway adapter 6, the light emitting unit 52 and the light receiving unit 53 are positioned straddling the two window portions 63 of the airway adapter 6. The infrared light for measurement emitted from the light emitting unit 52 crosses the measurement flow path 61 from one window portion 63 of the airway adapter 6 to the other window portion 63, and is received by the light receiving unit 53. Since the infrared light is absorbed by carbon dioxide in the measurement flow path 61, the light receiving unit 53 obtains a received light amount corresponding to a carbon dioxide concentration in the respiratory air passing through the measurement flow path 61. Data of the received light amount is sent to the patient monitor M via the wiring 51, the carbon dioxide concentration is calculated, and a measured value is monitored.

Unlike the airway adapter 4 according to the known embodiment, in the airway adapter 6 according to Embodiment 1, the opening 625 is provided at a lower portion of the measurement flow path 61 in a state where the airway adapter 6 is placed. FIG. 6 is a cross-sectional view of the airway adapter 6 before the opening 625 is closed. The water absorption member 64 is illustrated below the opening 625. The water absorption member 64 is exposed to an outside, and is configured to discharge water to the outside. The water absorption member 64 is made of a porous member having fine spaces through which water permeates. This member allows water to permeate and pass therethrough, but hardly allows a gas such as the respiratory air to pass therethrough.

Further, in Embodiment 1, a groove-shaped storage portion 641 having a tapered structure including a tapered surface T is provided on an upper surface of the water absorption member 64. The storage portion 641 is provided as a groove along an extending direction of the measurement flow path 61. The storage portion 641 is configured to store water generated by condensation, and the stored water penetrates the water absorption member 64.

As indicated by an arrow in FIG. 6, the opening 625 is closed by the water absorption member 64. In Embodiment 1, the water absorption member 64 is fixed in a vicinity of the opening 625 by adhesion, and the opening 625 is closed by the water absorption member 64 as illustrated in FIG. 4 and FIG. 5. FIG. 5 illustrates a state in which water W is accumulated in the storage portion 641. Water that cannot be immediately absorbed by the water absorption member 64 accumulates in the storage portion 641. Since the water absorption member 64 may include the storage portion 641 and has the tapered structure, a water absorption surface can be enlarged.

The water condensed in the measurement flow path 61 of the airway adapter 6 or the tubes in a vicinity thereof penetrates the water absorption member 64 at the lower portion of the measurement flow path 61 in a state where the airway adapter 6 is placed. A part of the water absorption member 64 is exposed to an outside of the airway adapter 6, and the permeated water is discharged from the water absorption member 64 to the outside. In a case in which a large amount of water is discharged, the water can be absorbed and evaporated by laying a gauze or the like under the water absorption member 64. Further, in a case in which an amount of condensation is small, the water can also be directly evaporated from an outer portion of the water absorption member 64 by providing the airway adapter 6 in a state of floating from the bed B.

First Modification

Figure 7:
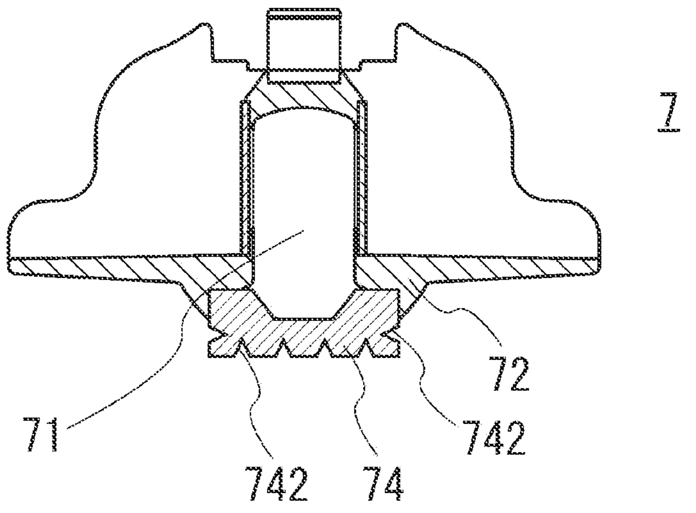
FIG. 7 is a cross-sectional view of an airway adapter according to a first modification of Embodiment 1.

FIG. 7 is a cross-sectional view of an airway adapter 7 according to a first modification of Embodiment 1. FIG. 7 is a cross-sectional view taken along a plane corresponding to plane A-A in Embodiment 1 orthogonal to an extending direction of a measurement flow path 71. In the first modification, an uneven structure is provided in an outer portion of a water absorption member 74 attached to a lower portion of an adapter body 72. As illustrated in FIG. 7, grooves 742 are formed on a lower surface and a side surface of the outer portion of the water absorption member 74, along the extending direction of the measurement flow path 71. Other configurations are the same as those in Embodiment 1. The water absorption member 74 is exposed to the outside, and is configured to discharge water to the outside.

Since the outer portion of the water absorption member 74 has the uneven structure, a large surface area can be achieved, and a large evaporation amount from the water absorption member 74 can be achieved. The uneven structure is not limited to grooves along the extending direction of the measurement flow path 71, and may be grooves orthogonal to the extending direction of the measurement flow path 71, grooves obliquely intersecting the extending direction of the measurement flow path 71, or a dot-shaped uneven structure.

Second Modification

Figure 8:
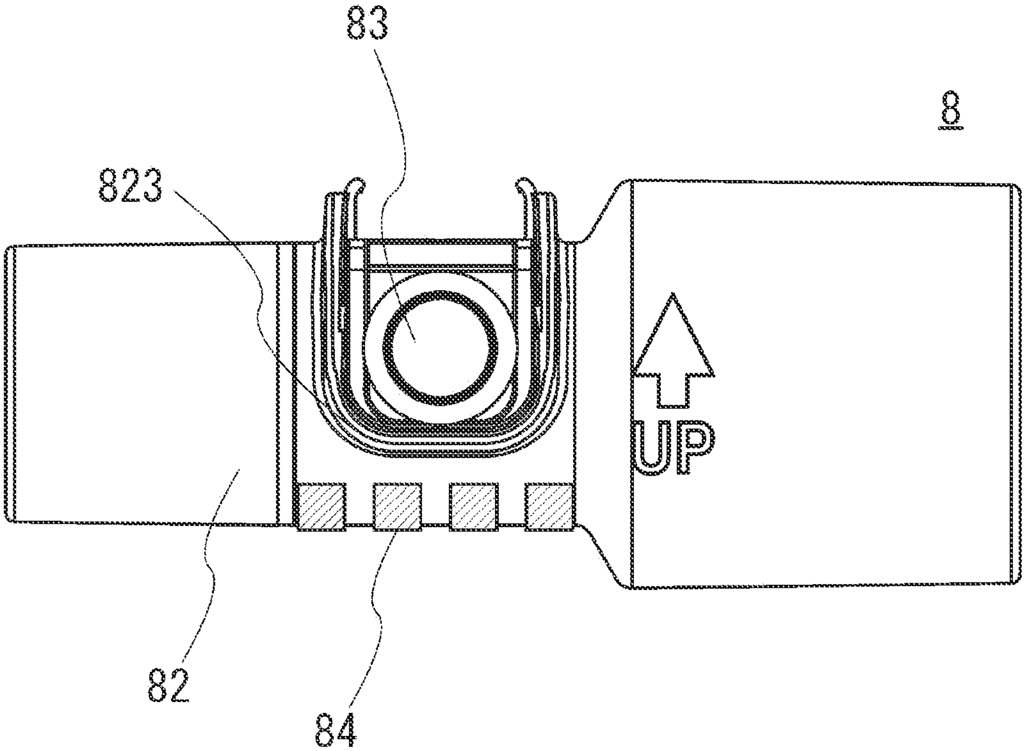
FIG. 8 is a side view of an airway adapter according to a second modification of Embodiment 1.

FIG. 8 is a side view of an airway adapter 8 according to a second modification of Embodiment 1. The airway adapter 8 according to the second modification is provided with a plurality of openings, and each opening is closed by a water absorption member 84. An adapter body 82 is provided with a window portion 83 and four openings below a sensor holding portion 823. The water absorption member 84 is fixed by adhesion to the four openings below the sensor holding portion 823. The water absorption member 84 is exposed to the outside, and is configured to discharge water to the outside. In the second modification, the four openings and the water absorption members 84 are arranged in an axial direction of the airway adapter 8, and may be provided in another form. For example, the four openings and the water absorption members 84 may be arranged in a direction perpendicular to an axis, or may be arranged in a polka-dot pattern along the axis of the adapter body 82 and in a direction perpendicular to the axis.

Embodiment 2

Figure 9:
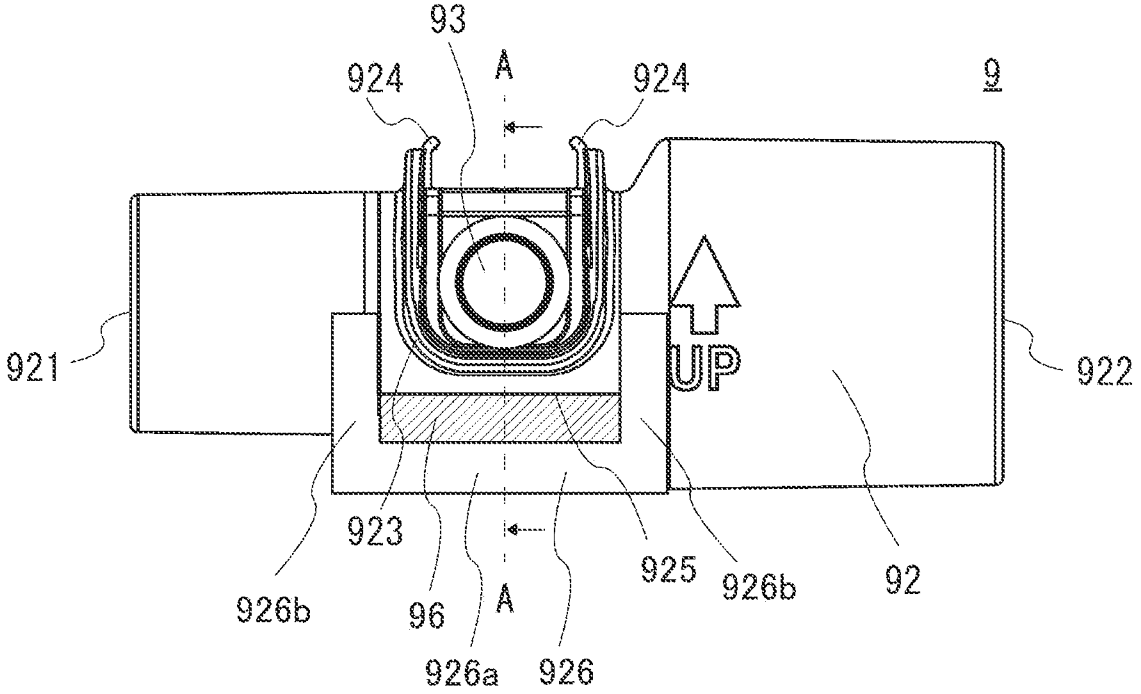
FIG. 9 is a side view of an airway adapter according to Embodiment 2.
Figure 10:
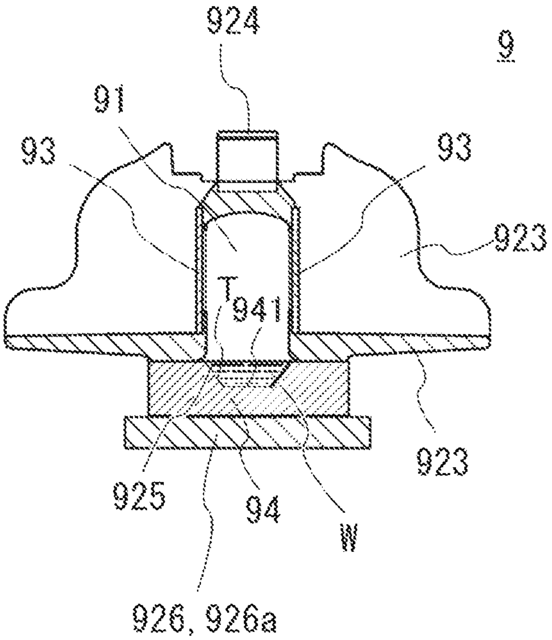
FIG. 10 is a cross-sectional view of the airway adapter according to Embodiment 2.

FIG. 9 and FIG. 10 illustrate an airway adapter 9 according to Embodiment 2. FIG. 9 is a side view of the airway adapter 9 according to Embodiment 2. FIG. 10 is a cross-sectional view taken along plane A-A in FIG. 9, and illustrates a state viewed from a direction of an arrow in FIG. 9. The airway adapter 9 is placed above the bed B substantially in a vertical direction illustrated in FIG. 9 and FIG. 10 in a state where the airway adapter is placed. The airway adapter 9 according to Embodiment 2 is connected and used as illustrated in FIG. 1, same or similarly to the airway adapter 4 according to the known embodiment and the airway adapter 6 according to Embodiment 1.

As illustrated in FIG. 9 and FIG. 10, the airway adapter 9 according to Embodiment 2 may include an adapter body 92 and window portions 93. As illustrated in FIG. 10, a sensor holding portion 923 sticks out both sides of the adapter body 92, and a measurement flow path 91 through which the respiratory air passes is formed inside the airway adapter 9. The measurement flow path 91 penetrates the adapter body 92 from a device side connection port 921 to a subject side connection port 922. Window portions 93 are provided on both sides of the measurement flow path 91. The adapter body 92 may have openings on both sides of the measurement flow path 91. A sheet-shaped infrared light transmission resin, which is a member through which the infrared light transmits, closes the openings to form the window portions 93. An opening 925 is provided in a lower portion of the measurement flow path 91 and is closed by a water absorption member 94. The water absorption member 94 is exposed to the outside, and is configured to discharge water to the outside. The above points are the same as those of the airway adapter 6 according to Embodiment 1.

FIG. 10 illustrates a state in which the water W is accumulated in a storage portion 941 including the tapered surface T. The water W is absorbed by the water absorption member 94 from the storage portion 941. The absorbed water is discharged from an external exposed surface on a lateral side of the water absorption member 94, and is evaporated.

On the other hand, unlike the airway adapter 6 according to Embodiment 1, in the airway adapter 9 according to Embodiment 2, a cover portion 926 is provided in a lower portion of the airway adapter 9. As illustrated in FIG. 9, the cover portion 926 may include leg portions 926*b* at two positions in a lower portion of the adapter body 92, and lower portions of the leg portions 926*b* are connected by a plate-shaped portion 926*a* to form a U-shape. The cover portion 926 and the opening 925 provided below the measurement flow path 91 are separated from each other, and the water absorption member 94 is fitted into a separated portion from a lateral side and is detachably fixed. Therefore, the water absorption member 94 can be easily fixed to the lower portion of the airway adapter 9 without using an adhesive.

Further, as illustrated in FIG. 10, in the airway adapter 9 according to Embodiment 2, a lateral width of the cover portion 926 is larger than a lateral width of the water absorption member 94. The cover portion 926 covers an entire lower surface of the water absorption member 94 with the plate-shaped portion 926*a* at a lower portion of the water absorption member 94. In the airway adapter 9 according to Embodiment 2, water is discharged by evaporation from a side surface of the water absorption member 94. Since the lateral width of the cover portion 926 is larger than the lateral width of the water absorption member 94, the fitted water absorption member 94 does not come into direct contact with the bed B, the sheet, or the like without laying a gauze or the like. By using the airway adapter 9 according to Embodiment 2, in a case where an amount of condensation inside the airway adapter 9 is small, the bed B or the like can be made difficult to get wet without laying a gauze or the like.

Third Modification

Figure 11:
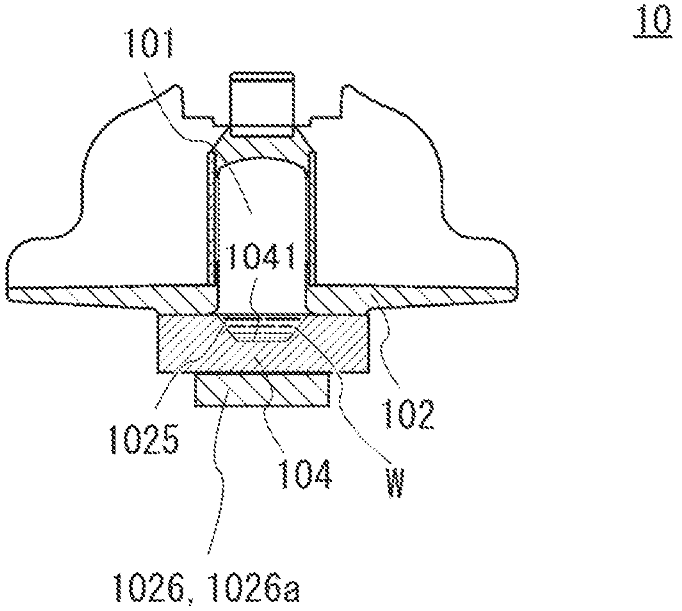
FIG. 11 is a cross-sectional view of an airway adapter according to a modification of Embodiment 2.

FIG. 11 is a cross-sectional view of an airway adapter 10 according to a third modification of Embodiment 2. Also in the airway adapter 10 according to the third modification, a plate-shaped portion 1026*a* of a cover portion 1026 is separated from an opening 1025 provided below a measurement flow path 101, and a water absorption member 104 is fitted from a lateral side. Further, same or similarly to Embodiment 2, the cover portion 1026 may include leg portions (not illustrated) at two positions in a lower portion of an adapter body 102, and lower portions of the leg portions are connected by a plate-shaped portion 1026*a* to form a U-shape. The water absorption member 104 is exposed to the outside, and is configured to discharge water to the outside.

FIG. 11 illustrates a state in which the water W is accumulated in a storage portion 1041 including the tapered surface T. The water is absorbed by the water absorption member 104 from the storage portion 1041. The absorbed water is discharged from an external exposed surface on a lateral side or a lower side of the water absorption member 104 and is evaporated, or is absorbed by a gauze or the like laid under the airway adapter 10. In the third modification, a lateral width of the cover portion 1026 is smaller than a lateral width of the water absorption member 104. The cover portion 1026 covers a part of a lower surface of the water absorption member 104 with the plate-shaped portion 1026*a* at a lower portion of the water absorption member 104. The other points are the same as those in Embodiment 2. In the third modification, the external exposed surface of the water absorption member 104 is large, water is easily discharged to the outside, and the water absorption member 104 is easily attached and detached.

Fourth Modification

Figure 12:
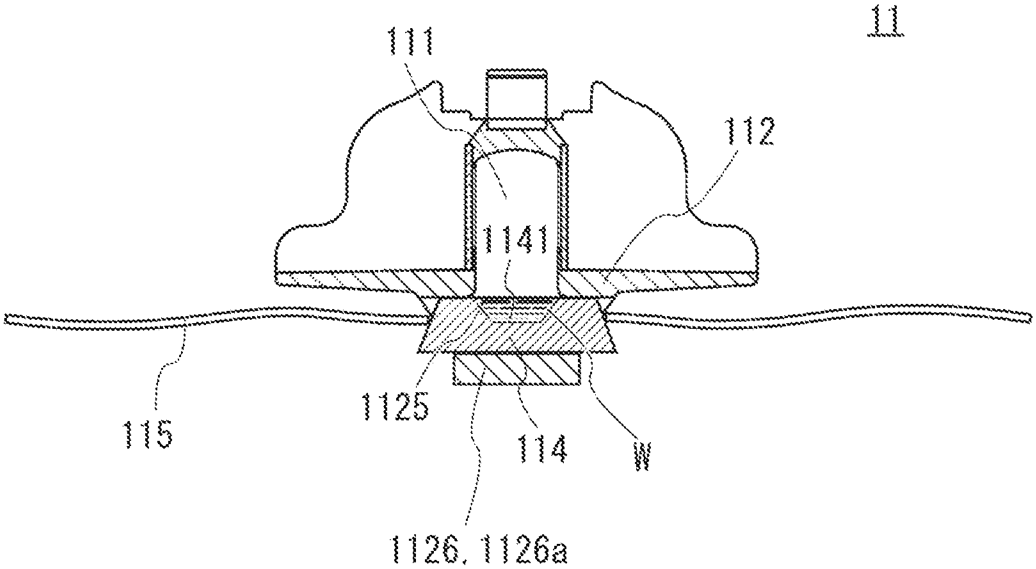
FIG. 12 is a cross-sectional view of an airway adapter according to another modification of Embodiment 2.

FIG. 12 is a cross-sectional view of an airway adapter 11 according to a fourth modification which is another modification of Embodiment 2. Also in the airway adapter 11 according to the fourth modification, a plate-shaped portion 1126*a* of a cover portion 1126 is separated from an opening 1125 provided below a measurement flow path 111, and a water absorption member 114 is fitted from a lateral side. Further, same or similarly to Embodiment 2, the cover portion 1126 may include leg portions (not illustrated) at two positions in a lower portion of an adapter body 112, and lower portions of the leg portions are connected by the plate-shaped portion 1126*a* to form a U-shape. The water absorption member 114 is exposed to the outside, and is configured to discharge water to the outside.

In the fourth modification, a replaceable evaporation sheet 115 is connected to the water absorption member 114. The evaporation sheet 115 is formed of a filter paper-like paper, and has a water absorption property. A rectangular hole into which the water absorption member 114 is to be fitted is provided near a center of the evaporation sheet 115. The water absorption member 114 according to the third modification is obtained by reducing a width of an upper portion of the water absorption member 104 of the airway adapter 10 according to the third modification illustrated in FIG. 11, and has a shape illustrated in FIG. 12. Further, the water absorption member 114 is covered with the evaporation sheet 115 having a hole from a lower side of the water absorption member 114, passed through the hole, and connected as illustrated in FIG. 12. Since the water absorption member 114 is in contact with the evaporation sheet 115, the water absorbed by the water absorption member 114 inside the airway adapter 11 penetrates the evaporation sheet 115. Then, the water permeated on a surface of the evaporation sheet 115 having a large surface area is evaporated.

Embodiment 3

Figure 13:
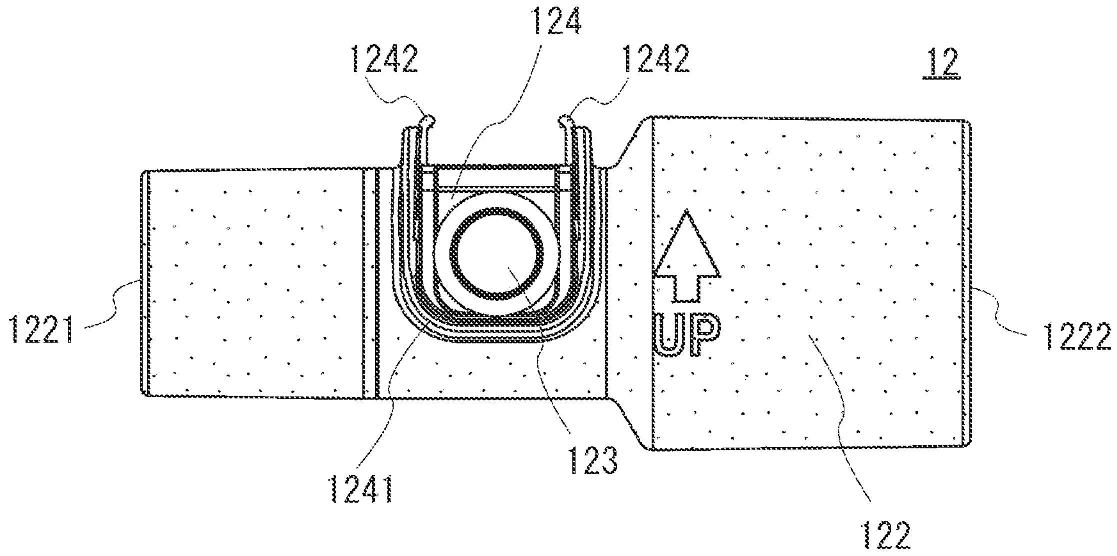
FIG. 13 is a side view of an airway adapter according to Embodiment 3.

FIG. 13 is a side view of an airway adapter 12 according to Embodiment 3. The airway adapter 12 according to Embodiment 3 is connected and used as illustrated in FIG. 1, same or similarly to the airway adapter 4 according to the known embodiment, the airway adapter 6 and the airway adapter 9 according to Embodiment 1 and Embodiment 2, and the airway adapter 7, the airway adapter 8, the airway adapter 10, and the airway adapter 11 according to the modifications.

In the airway adapter 12 according to Embodiment 3, an adapter body 122 is made of fired diatomaceous earth which is a porous member. A plastic sensor attachment portion 124 is fixed to the adapter body 122. The sensor attachment portion 124 may include a sensor holding portion 1241 extending laterally and locking projections 1242 provided at two upper positions, and the optical sensor 5 can be detachably mounted. Same or similarly to other embodiments, a measurement flow path (not illustrated) from a device side connection port 1221 to a subject side connection port 1222 is formed inside the airway adapter 12. The adapter body 122, which is a water absorption member, may have openings on both sides of the measurement flow path, and forms window portions 123 by closing the openings with a sheet-shaped infrared light transmission resin, which is a member through which the infrared light transmits.

Since the adapter body 122 is made of fired diatomaceous earth which is a porous member, the adapter body 122 serves as a water absorption member as a whole, and the measurement flow path is provided inside the water absorption member. The water in the measurement flow path can be discharged by the condensation water penetrating the adapter body 122 from the measurement flow path inside the airway adapter 12 and the water evaporating from the entire outer surface of the adapter body 122. The water absorption member formed as the adapter body 122 is exposed to the outside, and the water can be discharged to the outside.

In Embodiment 3, the plastic sensor attachment portion 124 is fixed to the water absorption adapter body 122, and a periphery of the window portion 123, the sensor attachment portion 124, and the like are made of plastic. However, some or all of these may be formed as a water absorption member and integrated with the adapter body 122.

In the above detailed description of the presently disclosed subject matter, it is assumed that the airway adapter is used for a patient. However, the airway adapter may be used for a subject other than a patient. As long as the optical sensor can be blocked such that the respiratory air does not leak, the window portion may be kept open without being blocked by a member through which the infrared light transmits. Further, the airway adapter may perform a measurement or the like other than the carbon dioxide concentration.

A groove forming the storage portion 641 and the like above the water absorption member 64 and the like in Embodiment 1 and Embodiment 2 and the modifications may extend over an entire width of the measurement flow path or may be formed in a part of the width. A shape of the groove may be a quadrangular prism having a trapezoidal side surface, such as the storage portion 641, or may be a long quadrangular shape. Further, a plurality of grooves may be formed. A plurality of recesses may be formed in the water absorption member instead of the grooves such as the storage portion 641. Further, the water absorption member may be a prism having no recess such as a groove on the upper surface.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An airway adapter comprising:

a first tube connection port configured to connect to a first tube;

a second tube connection port configured to connect to a second tube; and a measurement flow path formed between the first tube connection port and the second tube connection port and through which at least one of expired air or inhaled air of a subject passes through, wherein a water absorption member is provided in a lower portion of the measurement flow path in a state where the airway adapter is placed, wherein the water absorption member is exposed to an outside, and is configured to discharge water to the outside, and wherein the measurement flow path passes between opposed window portions of a member through which infrared light is transmitted.

2. The airway adapter according to claim 1, wherein an opening portion is provided in a lower portion of the measurement flow path in a state where the airway adapter is placed, and wherein the water absorption member is configured to close the opening portion to discharge the water to the outside.

3. The airway adapter according to claim 2, wherein the water absorption member includes a storage portion having a groove shape.

4. The airway adapter according to claim 3, wherein the storage portion is provided with a tapered structure.

5. The airway adapter according to claim 1, wherein a cover portion configured to cover a part of or all of the water absorption member is provided in a lower portion of the water absorption member.

6. The airway adapter according to claim 2, wherein the water absorption member is detachably attached to the opening portion.

7. The airway adapter according to claim 1, wherein the water absorption member is a porous member.

8. The airway adapter according to claim 1, wherein the water absorption member has an uneven structure on an outer portion of the water absorption member.

9. The airway adapter according to claim 1, wherein the water absorption member is connected to an evaporation sheet on an outer portion of the water absorption member.

10. The airway adapter according to claim 9, wherein the evaporation sheet is replaceable.

11. The airway adapter according to claim 2, wherein a plurality of opening portions including the opening portion are provided.

12. The airway adapter according to claim 2, wherein one opening portion is provided.

13. The airway adapter according to claim 1, wherein the measurement flow path is provided inside the water absorption member.

14. The airway adapter according to claim 1, wherein the water absorption member axially corresponds to the opposed window portions along the measurement flow path.

* * * * *